(12) United States Patent
Anderson et al.

(10) Patent No.: US 7,926,489 B2
(45) Date of Patent: Apr. 19, 2011

(54) PENILE COMPRESSION DEVICE

(75) Inventors: David W. Anderson, Brooklyn Park, MN (US); Gerald W. Timm, Minneapolis, MN (US); Claire Yang, Seattle, WA (US)

(73) Assignee: GT Urological, LLC, Minneapolis, MN (US)

( * ) Notice: Subject to any disclaimer, the term of this patent is extended or adjusted under 35 U.S.C. 154(b) by 211 days.

(21) Appl. No.: 12/248,404

(22) Filed: Oct. 9, 2008

(65) Prior Publication Data

US 2009/0036729 A1    Feb. 5, 2009

Related U.S. Application Data

(63) Continuation-in-part of application No. 11/122,395, filed on May 5, 2005, now Pat. No. 7,658,194.

(60) Provisional application No. 60/569,178, filed on May 7, 2004.

(51) Int. Cl.
*A61F 5/48* (2006.01)
(52) U.S. Cl. .................. 128/885; 128/DIG. 25
(58) Field of Classification Search .......... 128/885, 128/DIG. 25, 912; 600/29, 38–39, 41
See application file for complete search history.

(56) References Cited

U.S. PATENT DOCUMENTS

| | | | |
|---|---|---|---|
| 1,410,339 A | 3/1922 | Martinka | |
| 1,728,322 A | 9/1929 | Badrian | |
| 2,513,971 A | 7/1950 | Skinner | |
| 2,833,291 A | 5/1958 | Campagna | |
| 3,063,487 A | 11/1962 | Mullin | |
| 3,155,096 A | 11/1964 | Ourwin | |
| 3,866,611 A | 2/1975 | Baumrucker | |
| 3,926,175 A | 12/1975 | Allen et al. | |
| 4,139,007 A | 2/1979 | Diamond | |
| 4,534,353 A | 8/1985 | De Leur et al. | |
| 4,589,877 A | 5/1986 | Sivilich | |
| 4,800,900 A | 1/1989 | French | |
| 4,880,016 A | 11/1989 | Worth et al. | |
| 4,886,509 A | 12/1989 | Mattsson | |

(Continued)

FOREIGN PATENT DOCUMENTS

DE    201 12 864 U1    11/2001

(Continued)

OTHER PUBLICATIONS

Office Action in European Patent Application No. 07 761 680.3, issued by the European Patent Office Feb. 9, 2010, 2 pages.

(Continued)

*Primary Examiner* — Patricia M Bianco
*Assistant Examiner* — Camtu T Nguyen
(74) *Attorney, Agent, or Firm* — Hamre, Schumann, Mueller & Larson, P.C.

(57) ABSTRACT

A penile compression device for preventing urinary leaking and method for the same. First and second semi-rigid support arm are connected at opposing ends in their length direction. The support arms are biased towards each other in a resting position. The support arms are compressible from the length direction such that the support arms deform away from each other. An open region is formed between the support arms when the support arms are deformed, and enables penis insertion between the support arms. Releasing compression of the support arms enables the support arms to bias from a deformed position to a clamped position, whereby the support arms compress a male urethra to prevent urinary leakage. An absorbent sleeve may be affixed to the support arms to capture and hold any urine leakage.

13 Claims, 14 Drawing Sheets

U.S. PATENT DOCUMENTS

| | | | |
|---|---|---|---|
| 4,942,886 | A | 7/1990 | Timmons |
| 5,184,629 | A | 2/1993 | Erickson et al. |
| D339,418 | S | 9/1993 | Flynn |
| 5,249,437 | A | 10/1993 | Cole, Jr. |
| 5,327,910 | A | 7/1994 | Flynn |
| 5,342,332 | A | 8/1994 | Wheeler |
| 5,415,179 | A | 5/1995 | Mendoza |
| 5,474,572 | A | 12/1995 | Hayhurst |
| 5,554,149 | A | 9/1996 | O'Donnell |
| 5,571,125 | A | 11/1996 | Chadwick |
| 5,618,279 | A | 4/1997 | Pudlo |
| 5,702,381 | A | 12/1997 | Cottenden |
| 5,727,568 | A | 3/1998 | Kiser |
| 5,888,188 | A | 3/1999 | Srougi et al. |
| 6,026,813 | A | 2/2000 | Wilhelm |
| 6,039,750 | A | 3/2000 | Kubalak et al. |
| 6,105,174 | A | 8/2000 | Nygren et al. |
| 6,129,718 | A | 10/2000 | Wada |
| 6,131,576 | A | 10/2000 | Davis |
| 6,149,636 | A | 11/2000 | Roe et al. |
| 6,209,142 | B1 | 4/2001 | Mattsson |
| 6,223,751 | B1 | 5/2001 | Park |
| 6,234,174 | B1 | 5/2001 | Cheng et al. |
| 6,289,895 | B1 | 9/2001 | Cheng et al. |
| 6,338,729 | B1 | 1/2002 | Wada et al. |
| 6,349,727 | B1 | 2/2002 | Stewart, Jr. |
| 6,463,932 | B1 | 10/2002 | Single et al. |
| 6,609,522 | B2 | 8/2003 | Cheng et al. |
| 6,896,651 | B2 | 5/2005 | Gross et al. |
| 2002/0111640 | A1 | 8/2002 | Krause et al. |
| 2002/0153014 | A1 | 10/2002 | Cheng et al. |
| 2003/0004478 | A1 | 1/2003 | Mattsson |
| 2004/0173219 | A1 | 9/2004 | Bakane |
| 2005/0256365 | A1 | 11/2005 | Timm et al. |
| 2006/0149196 | A1 | 7/2006 | Bjornberg et al. |
| 2008/0011310 | A1 | 1/2008 | Anderson et al. |

FOREIGN PATENT DOCUMENTS

| | | |
|---|---|---|
| EP | 0 292 162 A | 11/1988 |
| FR | 2 638 964 A1 | 5/1990 |
| KR | 20-1993-25674 U | 11/1993 |
| KR | 20-0182741 Y1 | 6/2000 |

OTHER PUBLICATIONS

Supplementary European Search Report of European Application No. 07 76 1680, dated Jun. 4, 2009.

Moore et al. "Assessing Comfort, Safety, and Patient Satisfaction with Three Commonly Used Penile Compression Devices." Urology, vil. 63(1), Jan. 2004, pp. 150-154.

Written Opinion of the International Searching Authority of PCT/US2007/067931, dated Aug. 24, 2007.

International Search Report for application No. PCT/US2009/060157, dated Apr. 29, 2010 (3 pages).

Written Opinion of the International Searching Authority for application No. PCT/US2009/060157, dated Apr. 29, 2010 (3 pages).

Office Action for Chinese application No. 200780015949.7, dated Apr. 13, 2010 (7 pages).

International Search report for application No. PCT/US2005/015974, dated Jan. 3, 2007 (2 pages).

Written Opinion of the International Searching Authority for application No. PCT/US2005/015974, dated Jan. 3, 2007 (4 pages).

Office Action for Chinese application No. 200580021928.7, dated Feb. 20, 2009 (4 pages).

Supplementary European Search Report for corresponding application No. 05746796.1. dated May 25, 2009

PENILE COMPRESSION DEVICE

CROSS REFERENCE TO RELATED APPLICATIONS

The present application is a continuation-in-part application of U.S. application Ser. No. 11/122,395, which is now U.S. Pat. No. 7,658,194, entitled "Penile Compression Device" filed on May 5, 2005, which claims the benefit of U.S. Provisional Patent Application Ser. No. 60/569,178, filed May 7, 2004, and entitled "External Penile Compression Clamp with Absorbent Attachment", both of which are herewith incorporated by reference in their entirety.

FIELD

The disclosure herein relates to a penile compression device. More particularly, the disclosure herein relates to a penile compression device and method for the same that externally clamps the penis to prevent urinary leakage.

BACKGROUND

Penile compression clamps are well known and widely used to prevent urine leakage. In particular, penile clamps have been applied externally onto the penis for clamping the same. Such external penile clamps have been produced both as long-term reusable devices and also as short-term devices limited to one-week use. Typically, such devices have been employed for use in the inspection and treatment of diseases, wounds and other abnormal conditions of the bodies of humans and lower animals.

For example, Bard, Inc. produces the Cunningham clamp. The Cunningham clamp provides two pivoting arms connected by a single-hinge. Clamp arm surfaces that face the penis are padded for intended comfort. The Cunningham employs a ratcheted latch to clamp the two arms closer together and compress the penis. This clamp is reported to be a reusable, however, the large clamping forces often lead to pain, swelling and penile skin break down.

The Squeezer Klip™ disclosed in U.S. Pat. No. 6,463,932 provides a padded top and bottom arm in a pivoting configuration. Like the Cunningham, the Squeezer Klip™ is a hinged, reusable clamp. The dorsal and ventral arms include pressure-applying projections intended to contact the urethra, and preferentially apply pressure between the dorsal veins and arteries. The Squeezer Klip™ avoids direct compression of the neurovascular bundle. Patients are often incapable, however, of repeatedly applying the pressure-applying projections to the appropriate location to effect urethral closure. A screw mechanism clamps the penis using a fine compression adjustment via a threaded adjustment knob. The screw mechanism, however, requires a higher degree of manual dexterity to adjust compression, which can be difficult for older arthritic men.

The C3 clamp disclosed in U.S. Pat. No. 5,184,629 provides a clamp intended for use that is limited to approximately one week. The C3 is constructed from a co-extruded and thermoformed polyolefin sheet. The resultant component has two clam shelled halves connected by a hinge. The penis is placed through a portal between the two halves and the halves are folded over to compress the penis. The clam shells are held closed by a Velcro® strap. Force is localized on the urethra by presence of a raised bump on the bottom clam shell half. The C3 is available in only two fixed sizes. As there is great penile anatomical variation requiring multiple clamp sizes, a clamp frequently may be improperly selected. Further, the ability to operate the strapping system is often difficult for older, arthritic men. Such inconsistencies in sizing and the user dependent strapping system, however, make the C3 less reliable in its ability to control leakage.

None of the clamps above entirely eliminated urinary leakage.

Other clamps have been disclosed in U.S. Pat. Nos. 6,609,522, 6,289,895 B1, 6,609,522 B2, and 6,234,174 B1. These patents, however, provide detailed straps, latches, hinges and mechanisms for "dialing" in required urethral pressure. Experience with the C3 and such clamps indicate that users may be confused by the added complexity of such components.

While these clamps provide some advancement for controlling urinary dysfunction and protecting against bladder malfunction, improvements may yet be made to penile compression devices for males experiencing stress urinary incontinence. There is need for a penile compression device that provides optimum comfort and that is easy to apply and remove, while sufficiently preventing urinary leakage. Improvements may still be made to a penile compression device that provides an absorbent mechanism conveniently and comfortably attached to the compression device.

SUMMARY

It is a purpose of the present disclosure to overcome these difficulties, thereby providing an improved penile compression device. The penile compression device provides a semi-rigid clamp compressible from an initial rest position. Manual compression of the clamp causes shape deformation of the clamp arms forming an open region within the clamp that is appropriate for penis insertion. Releasing compression allows the clamp to bias back toward the rest position and into a clamp position. In the clamp position, biasing by the clamp sufficiently compresses the male urethra to prevent urinary leakage.

In one embodiment, a penile compression device includes semi-rigid first and second support arms connected at opposing ends of their length direction. The support arms are biased toward each other in a resting position, such that a penis may not be inserted therebetween. The support arms are manually compressible from the length direction. Manual compression causes shape deformation of the support arms to form an open region between the support arms and appropriate for penis insertion. Releasing clamp compression allows the support arms to bias to a clamp position. In the clamp position, biasing by the first and second support arms compresses the male urethra to prevent urinary leakage.

In one preferred embodiment, the first and second semi-rigid support arms are integrally formed as a single piece, closed biasing structure. The support arms are preformed as a single injection molded plastic structure.

In another embodiment, one of the first and second semi-rigid support arms includes an occlusive protrusion disposed on the side surface thereof. The occlusive protrusion concentrates compression on a male urethra from the biased support arms.

In another preferred embodiment, each of the first and second semi-rigid support arms includes padded foam disposed on the side surfaces thereof.

In yet another embodiment, the first and second support arms are connected by a hinge connection disposed at each of the opposing ends.

In yet another preferred embodiment, the first and second support arms define a two-piece, closed biasing structure. Preferably, the first and second support arms each define an injection molded material. More preferably, the injection molded material is a plastic material minimizing deformation.

In another embodiment, a penile compression device further comprises an absorbent attachment operatively connected to the first and second support arms, the absorbent attachment capturing and holding inadvertent urine leakage.

In yet another embodiment, a penile compression device further comprises a pressure concentrating insert. The pressure concentrating insert is surgically implanted on a dorsal urethral surface.

Preferably, penile compression device is externally applied to a user.

One embodiment of a method for preventing urinary leakage, includes providing a penile compression device above. The first and second support arms are compressed from opposing ends in the length direction, so as to deform the support arms. The first and second support arms are deformed to form the open region. A penis is inserted between the first and second support arms when the support arms are deformed. Compression of the support arms is released thereby enabling the support arms to bias from a deformed position to a clamp position, wherein the support arms bias the support arms toward each other to compress a male urethra.

In another embodiment, the method for preventing urinary leakage further comprises operatively connecting an absorbent attachment with the support arms. The absorbent attachment captures and holds any inadvertent urine leakage within the absorbent attachment.

In yet another embodiment, a method for preventing urinary leakage includes implanting a pressure concentrating insert at a dorsal urethral surface.

In other embodiments, various other structures can be implemented for a penile compression device and a method of urethral compression. For example, the support arms may be joined at their ends by flexible tapes, adhesives, thermal processes, end caps, or through constraint by the absorbent attachment itself.

The simple use of manual compression and decompression to deform and relax the penile compression device of the present application is in sharp contrast to other more complex clamping mechanisms. The Cunningham clamp, for example, requires the user to bend its compressive arms to a shape appropriate to their anatomy and then select a ratchet position to provide adequate compression. The C3 clamp requires that the penis be inserted into the portal between two clam shell halves and that the clamp be squeezed to apply an appropriate load while a Velcro® strap is wrapped around the clamp to secure its closure. The Squeezer Klip™ requires the user to operate a threaded adjustment knob to secure the appropriate penile compression.

The penile compression device of the present application provides suitable neurovascular load distribution that can be coupled with localized urethral compression. The penile compression device provides a universally fitting clamp that improves comfort while improving urine leakage prevention.

BRIEF DESCRIPTION OF THE DRAWINGS

Like reference numbers generally indicate corresponding elements in the Figures. The embodiments illustrated are exemplary only and are in accordance with the inventive principles described herein.

DETAILED DESCRIPTION

Figure 1A:
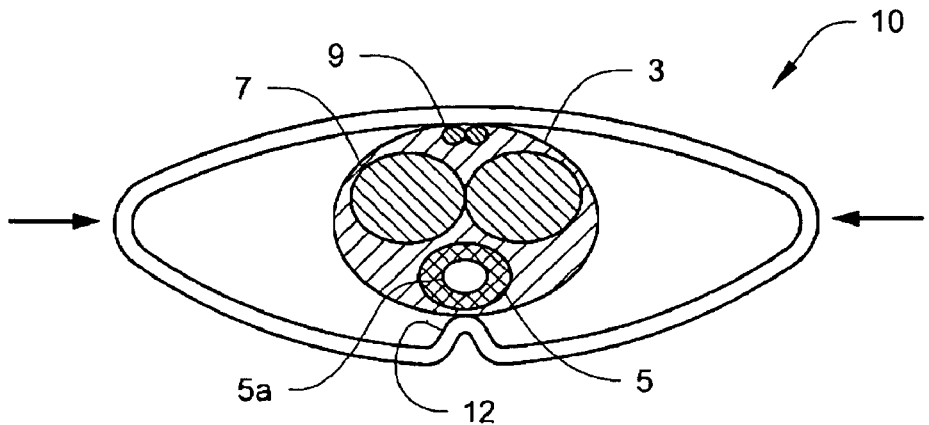
FIG. 1A represents an end view of one embodiment for a penile compression device. The device is shown applied to a penis illustrated in section where the device is not clamped.
Figure 1B:
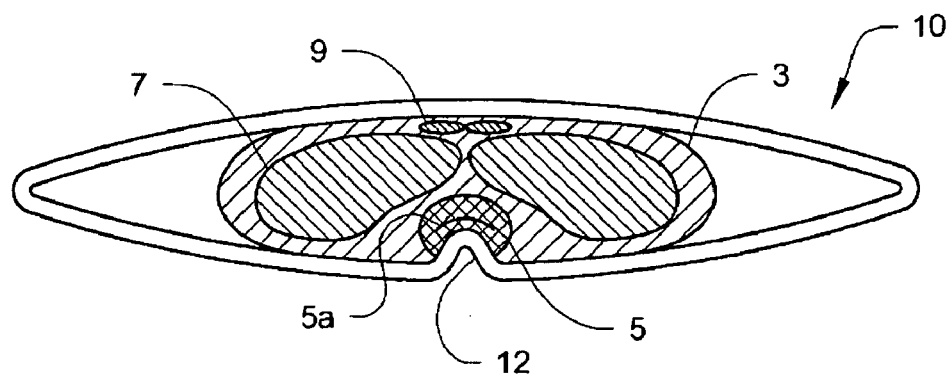
FIG. 1B represents an end view of the penile compression device shown in FIG. 1A. The device is shown applied to the penis illustrated in section where the device is clamped.
Figure 2:
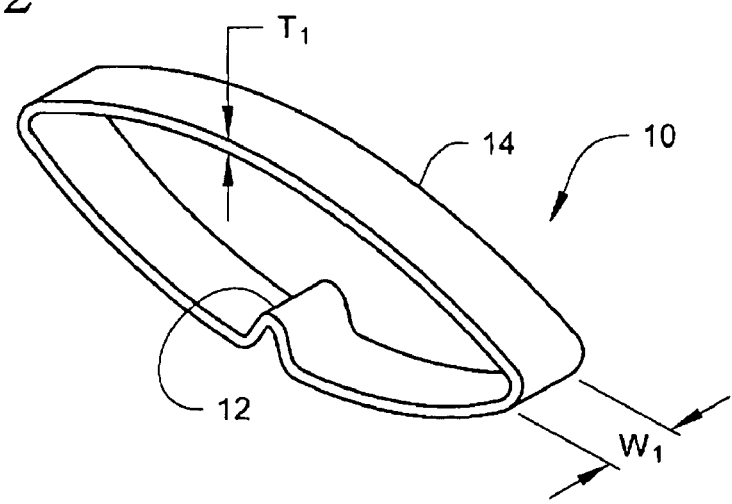
FIG. 2 represents a perspective view of the penile compression device of FIG. 1A.

One exemplary embodiment of a penile compression device 10 is provided in FIGS. 1A-2. As shown in FIGS. 1A-B, the penile compression device 10 is illustrated with a penis 3 (shown in section) inserted therethrough. As widely known, the penis 3 includes a urethra 5 and urinary pathway 5a. Other penile tissue is also shown including the corpora cavernosa 7 and the dorsal penile neurovascular bundle 9.

The penile compression device 10 includes a closed planar structure 14 defining oppositely disposed first and second support arms. The first and second arms define inner and outer side surfaces. As shown in FIGS. 1A-2, the first and second support arms resemble a top support arm proximate the dorsal penile neurovascular bundle 9 and a bottom support arm proximate urethra 5. It will be appreciated that either of the first or second support arms may be any of the top and bottom arms. Such top or bottom designations are for purposes of describing the illustrations only. The first and second support arms are connected at ends of a length direction thereof.

As shown in FIG. 2, the inner side surfaces of the support arms of the planar structure 14 bias toward each other in a resting position. The arrow directional of FIG. 1A illustrates the first and second support arms are compressible from the length direction, such that the inner side surfaces are deformable away from each other. An open region forms between the first and second support arms when the support arms are deformed. The open region enables penis 3 insertion between the first and second support arms when the support arms are deformed.

As shown in FIG. 1B, releasing compression of the support arms enables the support arms to bias from a deformed position back toward the rest position and into a clamp position, whereby the support arms bias the side surfaces toward each other. This action compresses the male urethra 5 preventing urinary leakage through the urinary pathway 5a.

Thus, in operation, manual compression of the penile compression device 10 across its sides causes shape deformation appropriate for insertion of the penis 3 into the open region. Releasing compression of the penile compression device 10 allows biasing toward a clamp position. In the clamp position, compression by the biased support arms is sufficient to prevent urinary leakage through the urethra 5.

An occlusive protrusion 12 may be disposed proximate the urethra 5 on one of the first or second support arms. Preferably, the occlusive protrusion 12 is disposed on the bottom support arm proximate the urethra 5. More preferably, the occlusive protrusion 12 is inwardly directed, and applies localized compression on the urethra 5 from the bottom surface of the penis 3.

Compressing the penile compression device 10 across its sides moves an occlusive protrusion 12 away from the urethra 5 to allow unobstructed urinary voiding through the urinary path 5a. Compression of the penile compression device 10 in the length direction also allows removal of the device 10 from the penis 3.

As shown in FIGS. 1A-2, the penile compression device 10 may be a one-piece, semi-rigid, and closed biasing structure as shown in FIGS. 1A-2. Preferably, the width W of the penile compression device 10 in contact with the top or dorsal surface of the penis 3 (See FIG. 2) may be maximized to distribute compressive loads and minimize the pressure applied to the penile tissue and underlying neurovascular bundle 9. High loads applied to the neurovascular bundle 9 can cause pain and reduced penile blood flow. The width W may be between 0.25 inches and 1.0 inch. It will be appreciated that these widths are merely exemplary, as other widths may be equally or more suitable.

The penile compression device 10 may be generally ovoid in shape with an occlusive protrusion 12 disposed on one of the first or second support arms. Human penile circumferences usually vary within a range of 6 cm to 14 cm. If required, several sizes may be employed to accommodate the varying penile circumferential sizes and to provide adequate urethral compression. The wall thickness T of the penile compression device 10 may be suitably varied as necessary for optimum structural stiffness. Thereby, optimum urethral compression can be provided, while not requiring a large manual force to deform the device 10 when operated.

The penile compression device 10 may be manufactured from semi-rigid thermoplastic materials. Such materials may include, but are not limited to Delrin® (Dupont, Inc.) or a polycarbonate (Entec, Inc.) using standard thermoplastic extrusion or injection molding practices. The penile compression device 10 may also be manufactured from a spring metal material. Such metal material may be, but is not limited to, a hardened 300 series stainless steel or 17-7PH stainless steel. To close the structure manufactured from steel sheets, standard sheet metal rolling practices or spot welds may be employed. It will be appreciated, however, that such named plastic and metal materials are exemplary only. Other materials including plastics, metals, and non-plastic and non-metal materials may be employed, and may be equally or more suitable. The materials for manufacture may be limited only to such materials having the physical characteristics contemplated for the penile compression device 10. Such contemplated physical characteristics include the necessary compression and biasing features for the support arms.

Figure 6A:
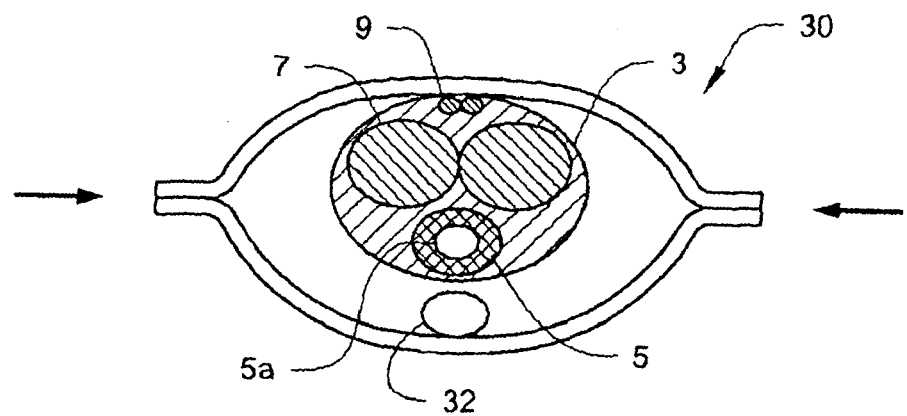
FIG. 6A represents an end view of another embodiment for a penile compression device. The device is shown applied to a penis illustrated in section where the device is not clamped.
Figure 6B:
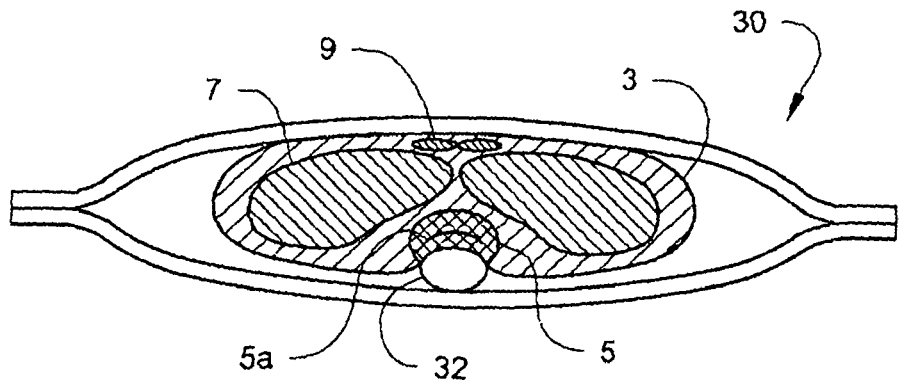
FIG. 6B represents an end view of the penile compression device shown in FIG. 6A. The device is shown applied to the penis illustrated in section where the device is clamped.
Figure 7:
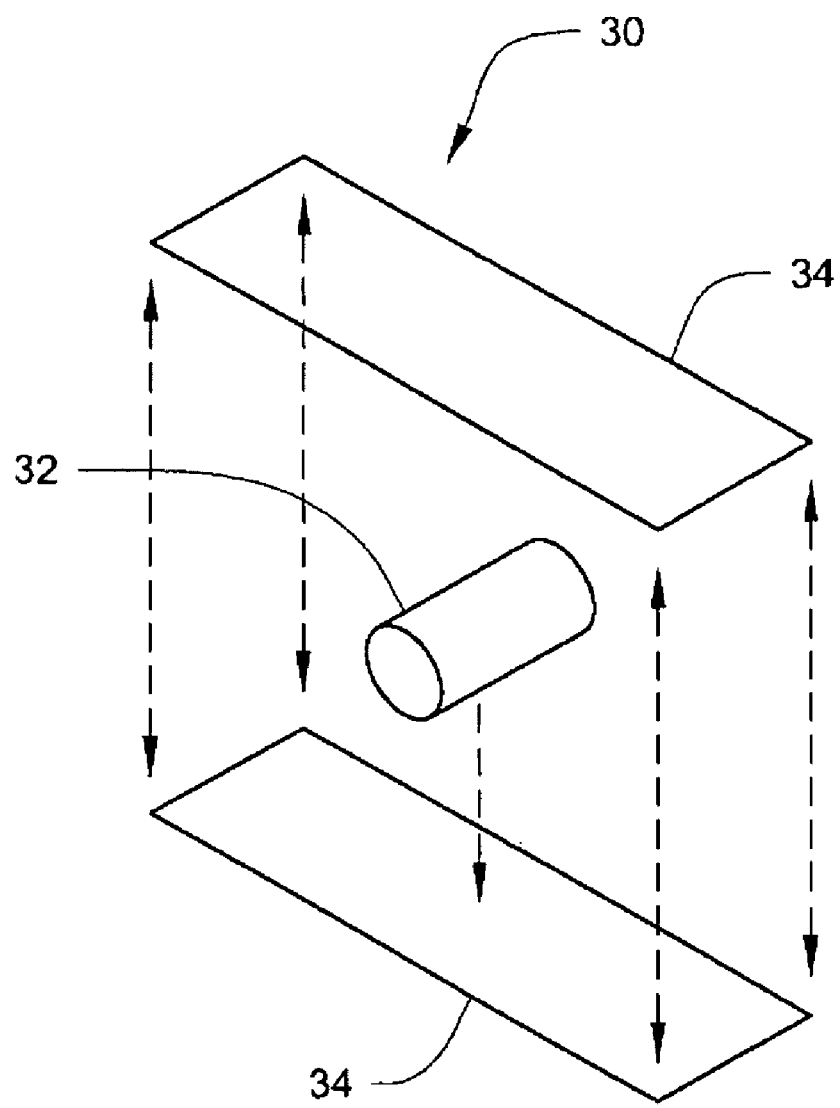
FIG. 7 represents an exploded perspective view of the penile compression device of FIG. 6A.

The penile compression device 30 may also be manufactured from multiple components to facilitate use of automated manufacturing processes as shown in FIGS. 6A-B and FIG. 7. The first and second support (top and bottom) arms 34 may be manufactured from thermoplastic or metal as described above. Preferably, the support arms 34 are shaped as planar strips. The occlusive protrusion 32 is joined to the bottom support arm. Preferably, the occlusive protrusion 32 is a cylindrical member having a width approximately equivalent to the width of the support arms 34. The top and bottom support arms 34 are then joined at their ends lengthwise. The first and second support arms 34 may be joined by use of adhesives, ultrasonic or thermal welding processes. It will be appreciated that these joining processes are exemplary only, as other joining methods may be equally or more suitable. The function and deformation of the penile compression device 30 is the same as previously described above.

In yet another embodiment, urethral compression may be further maximized by the surgical implantation of a pressure concentrating insert 19 on the lop or dorsal urethral surface. The pressure concentrating insert 19 provides a backing surface against which the occlusive protrusion 12 may compress the urethra 5.

Figure 3A:
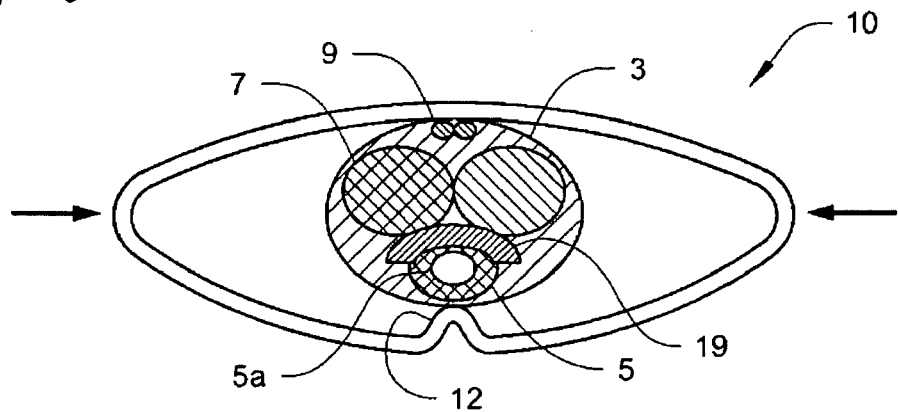
FIG. 3A represents a side view of the penile compression device of FIG. 1A. The device further illustrates one embodiment for an implanted pressure concentrating insert. The device is shown applied to the penis illustrated in section where the device is not clamped.
Figure 3B:
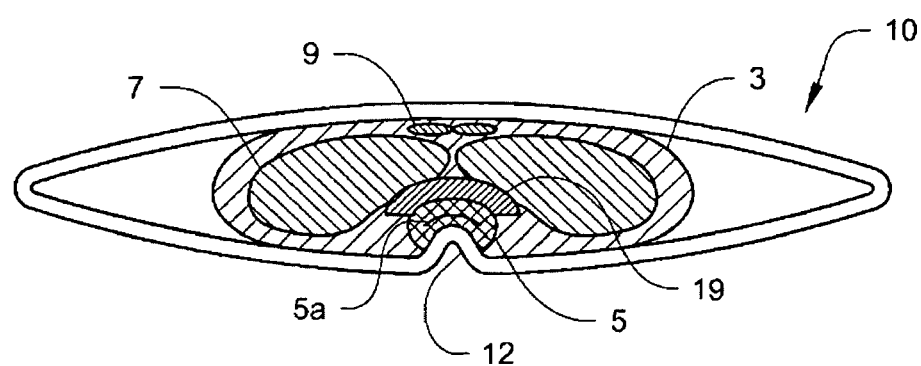
FIG. 3B represents a side view of the penile compression device of FIG. 1A and including the implanted pressure concentrating insert of FIG. 3A. The device is shown applied to the penis illustrated in section where the device is clamped.
Figure 3C:
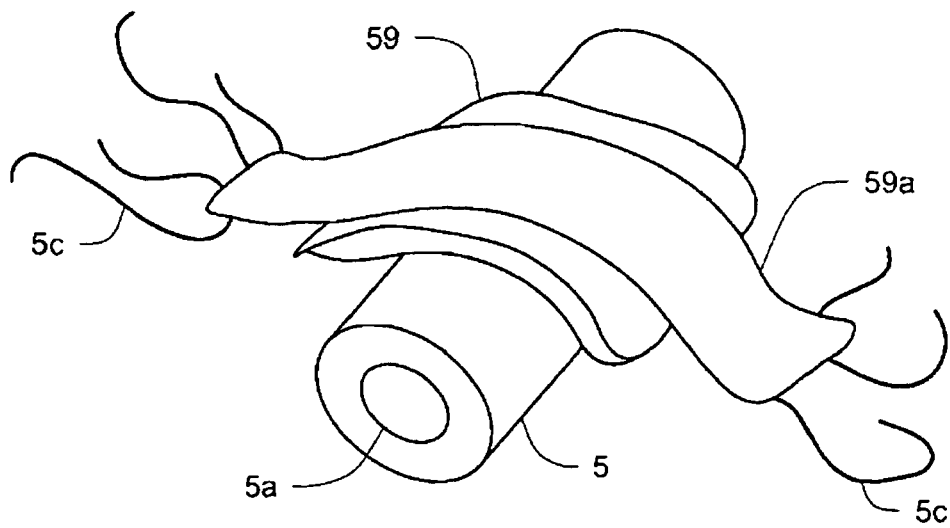
FIG. 3C represents another embodiment of an implanted pressure concentrating insert. The insert is illustrated in an implanted state.

FIGS. 3A-C illustrate the penile compression device 10 employed in conjunction with the surgical implantation of an exemplary embodiment for a pressure concentrating insert 19. The pressure concentrating insert 19 provides a surface or backing that assists the occlusive protrusion 12 in compression of the urethra 5. The surgically implanted pressure concentrating insert 19 is intended to provide a backstop, against which, the penile compression device 10 may compress the urethra 5. In this configuration, the pressure concentrating insert 19 can prevent the urethral tissue, namely the urethra 5, from moving away from the occlusive protrusion 12 and compress into the other more compliant penile tissue. It will be appreciated that surgical implantation of the pressure concentrating insert 19 can be accomplished by one of skill in the medical and surgical arts.

Preferably, the pressure concentrating insert 19 has an arcuate profile to conform to the shape of the dorsal urethral surface. However, the arcuate shape is exemplary only, as other shapes may be equally or more suitable.

The insert 19 may be manufactured from such rigid materials as 316 LVM stainless steel, 6Al 4V ELI titanium or silicone rubber with a durometer in excess of 35 Shore A. The pressure concentrating insert 19 may also be manufactured from softer more flexible materials such as silicone rubber with a durometer no greater than 35 Shore A. This would allow flexing of the insert 19 in response to normal bodily movement. Preferably, the length of the pressure concentrating insert along the urethral axis approximates the mating width of the occlusive protrusion 12 on the penile compression device 10. However, it will be appreciated that these named materials are exemplary only. Other materials may be used to produce the insert 19.

FIG. 3C also illustrates a pressure concentrating insert 59 in an implanted state and further showing surrounding penile tissue 5c. A segment 59a fixes the pressure concentrating insert 59 to the surrounding penile tissue 5c. Preferably, the segment 59a is a flexible material. The flexible material includes but is not limited to a polyester reinforced silicone sheeting adherent to the back of the pressure concentrating insert 59 to allow fixation of the insert 59 to surrounding penile tissues 5c. It will be appreciated that other materials, including semi-rigid or rigid materials, may be equally or more suitable.

Reported clinical experience still might indicate that total urine leakage protection is difficult for penile compression clamps. Thus, in another preferred embodiment of a penile compression device 10, an absorbent attachment 20 is attached to the penile compression device 10. As shown in FIGS. 4A-D, the absorbent attachment 20 is designed to contain the penis 3 in an opening 22 thereof. The absorbent attachment 20 absorbs any inadvertent trace or small amount of urine escaping the penis 3 during usage.

Figure 4A:
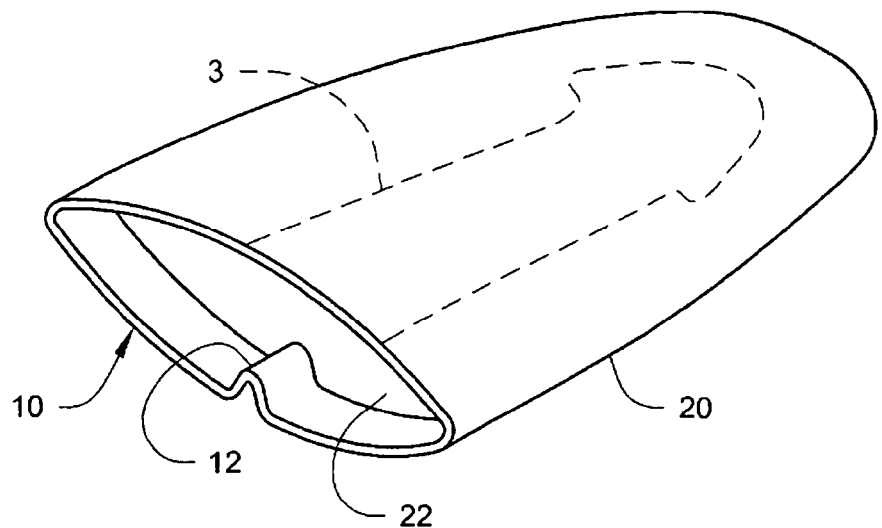
FIG. 4A represents a perspective view of the penile compression device of FIG. 1A and further including one embodiment of an absorbent attachment and one embodiment for affixing the penile compression device with the absorbent attachment.
Figure 4B:
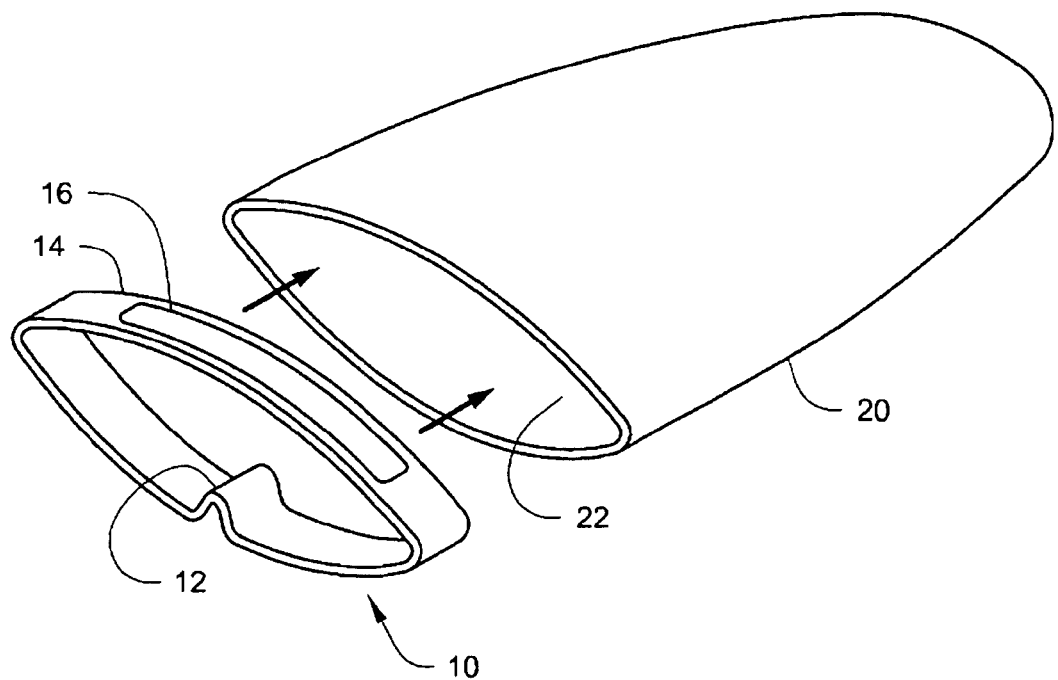
FIG. 4B represents an exploded perspective view of the penile compression device and absorbent attachment shown in FIG. 4A. The penile compression device is illustrated as being insertable into the absorbent attachment.

Preferably, the absorbent attachment 20 is an absorbent sleeve 20 slipped over the penis 3 and the penile compression device 10 following device 10 placement. In this instance, the sleeve 20 may be attached to the outer surface of the penile compression device 10 through use of an adhesive surface or strip or use of a Velcro® closure (FIGS. 4A-B).

Figure 4C:
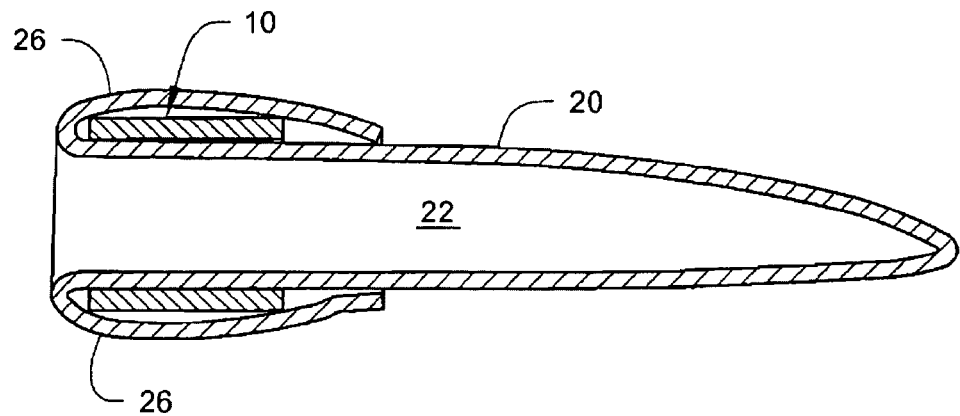
FIG. 4C represents a side sectional view of another embodiment for affixing the penile compression device with the absorbent attachment.

The absorbent sleeve 20 may be affixed to the penile compression device 10 at the time of manufacture by an adhesive, Velcro® closure or thermal weld (FIG. 4C). FIG. 4C illustrates an overlap 26 of the absorbent sleeve 20 and enclosing the penile compression device 10.

Figure 4D:
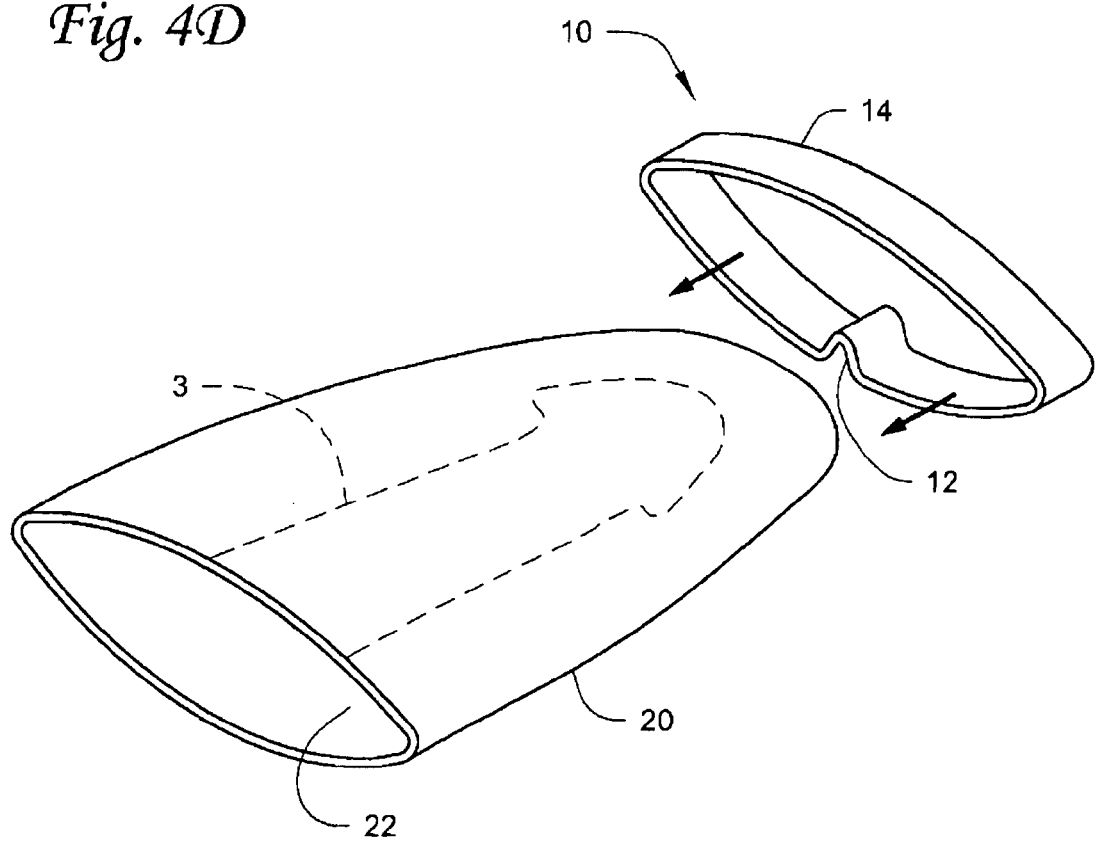
FIG. 4D represents a perspective view of yet another embodiment for affixing the penile compression device with the absorbent attachment.

The absorbent sleeve 20 may also be placed onto the penis 3 prior to placement of the penile compression device 10 (FIG. 4D). FIG. 4D illustrates an arrow directional for the penile compression device 10 to be slid over the absorbent sleeve 20. Subsequent penile compression device 10 placement will act to anchor the sleeve 20 to the penis 3.

Figure 5:
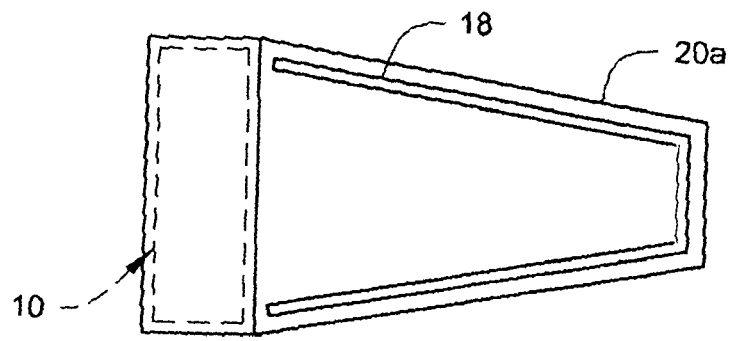
FIG. 5 represents a side plan view of yet another embodiment for an absorbent attachment.

FIG. 5 illustrates an absorbent sleeve 20a that is tapered along the penile axis and away from the penile compression device 10. In this configuration, the sleeve 20a profile is minimized, thereby reducing any unnecessary bulk, which must be concealed within undergarments. The minimized profile can help avoid discomfort for the user. It will be appreciated that the tapering grade or degree can be suitably varied to accommodate penile sizes.

Preferably, layers of absorbent material are joined to one another along bond surfaces 18, so as to form the sleeve 20a and necessary opening for receiving the penis 3. More preferably, two halves of absorbent and leak protectant material may be joined together at the bond surfaces 18. Joining processes may include, but are not limited to, adhesives, inclusive of hot melt adhesives, ultrasonic welds and other thermal welding processes. It will be appreciated, however, that such processes are exemplary only, as other methods may be equally or more suitable.

The absorbent sleeve 20, 20a may be manufactured from polyurethane open celled foams or polyolefin open celled foams such as Willsorb® manufactured by Illbruck, Inc. A water resistant barrier layer may be disposed and adherent to the outer surface of the foam that will prevent inadvertent leakage of any absorbed urine. The absorbent sleeve 20, 20a may also be manufactured from non-woven, absorbent paper with polyethylene barrier liners typically used in the construction of diapers. Sodium polyacrylate may be used with the nonwoven paper layers to further absorb urine. It will be appreciated that these materials are exemplary only, as other materials may be equally or more suitable as an absorbent and leak protectant.

Figure 8A:
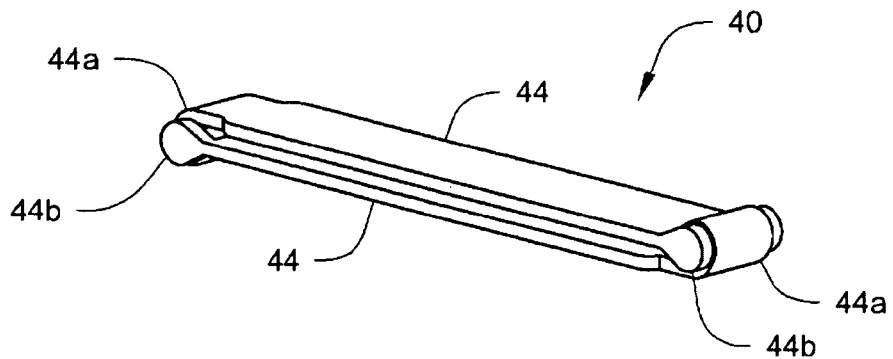
FIG. 8A represents a perspective view of yet another embodiment of a penile compression device.
Figure 8B:
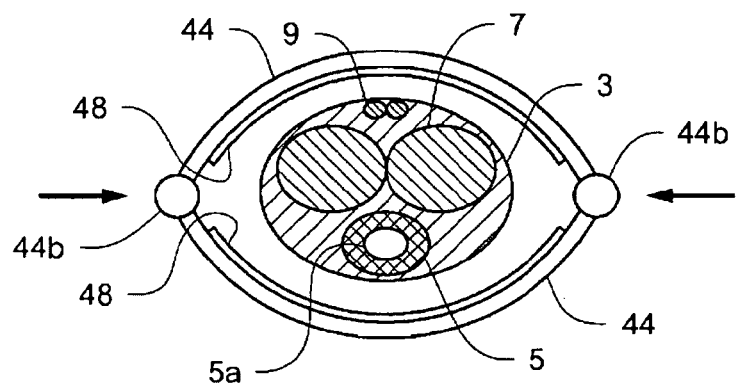
FIG. 8B represents an end view of the penile compression device of FIG. 8A. The penile compression device is shown applied to a penis illustrated in section where the device is not clamped.
Figure 8C:
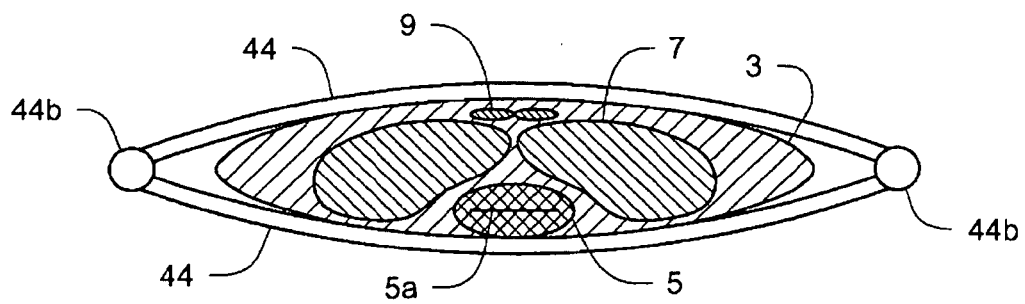
FIG. 8C represents an end view of the penile compression device shown in FIG. 8A. The device is shown applied to the penis illustrated in section where the device is clamped.
Figure 9:
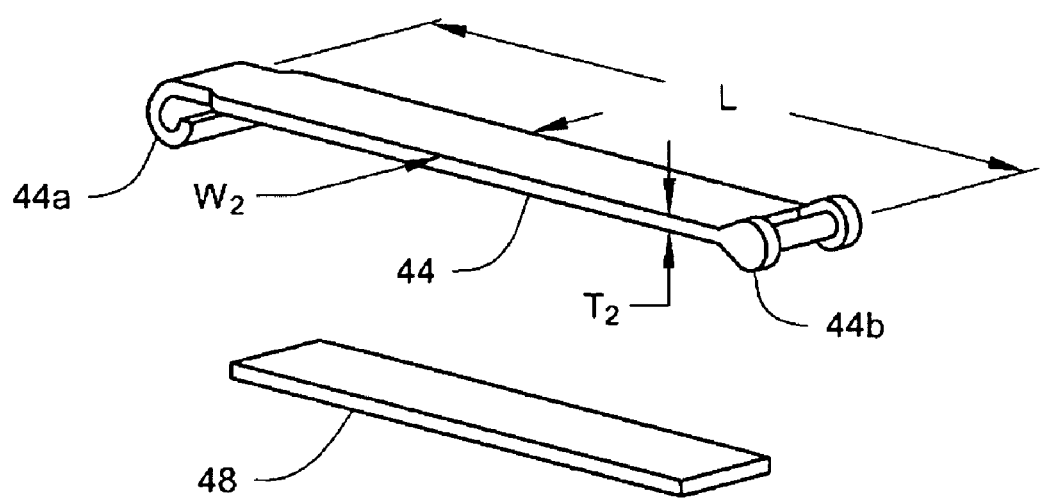
FIG. 9 represents a perspective view of one planar member of the penile compression device of FIG. 8A in an exploded state.

Clinical experience with the penile compression device 10 and absorbent attachment 20 might also indicate that an occlusive protrusion, as disclosed in the above, may not be necessary to prevent urinary leakage. FIGS. 8A-9 illustrate another preferred embodiment for a penile compression device 40. As shown in FIGS. 8A-8C, the support arms 44 of the device 40 are deformable away from each other and bias together. This configuration is similar to that described in the above embodiments. Differently, the penile compression device 40 defines a two-piece, hinged clamp construction. This construction helps prevent permanent deformation of the support arms 44, while enabling only temporary deformation and maximizing occlusive ability when in use.

The penile compression device 40 includes two support arms 44 that are hingedly connected by a hook portion 44a and hook pivot 44b. Preferably, the support arms 44 are connected by a hinge connection disposed at each of the opposing ends.

As shown in FIGS. 8A-9, each support arm 44 includes one hook portion 44a disposed on one end and one hook pivot 44b disposed on the other end. In this configuration, the two support arms 44 are connected such that the hook portion 44a from one support arm rotatably connects with the hook pivot 44b of the other support arm. The other hook portion 44b then rotatably connects with the other hook pivot 44b.

It will be appreciated that this configuration is exemplary only, as other configurations may be employed that are equally or more suitable. For example, one support arm 44 may include only hook portions 44a and the other support arm 44 may include only hook pivots 44b. It will also be appreciated that the hook/pivot structure is merely exemplary as other connective structures may be employed to mechanically connect the two support arms 44.

Preferably, the support arms 44 are snapped together. The penile compression device 40 may be used alone to compress the penis 3 or be operatively connected with an absorbent attachment such as 20, 20a described above. More preferably, each support arm 44 includes a layer or strip of padding material 48. Preferably, this padding material 48 is a closed or open celled polyolefin foam that adheres to the inner surface of each support arm 44 to maximize patient comfort. It will be appreciated that a variety of padding materials may be employed, and are not necessarily limited to a foam material.

The width, length and thickness of each support arm 44 may be altered to adjust the occlusive pressure applied to the penis 3 and urethra 5. Appropriate dimensions necessary to prevent urine leakage, yet maintain patient comfort, may include but are not limited to approximately a width of 0.5 inches, a length of 3.0 inches and a thickness of 0.05 inches. Preferably, the support arm 44 resembles a planar shape resembling a rectangular strip. The support arms 44 substantially define two straight planar members adjacently connected at ends of their length direction, and are temporarily deformable by compression from the ends. Releasing compression from the sides enables the support arms 44 to bias back toward its rest position shown in FIG. 8A.

More preferably, each support arm 44 of the penile compression device 40 may be injection molded from a thermoplastic such as HYLEX polycarbonate, which minimizes plastic deformation. As the support arms 44 are substantially straight planar members, employing such a material with this configuration prevents permanent deformation of the device 40. It will be appreciated, however, that the shape and manufacturing materials may be suitably varied as necessary to accomplish the physical characteristics of the device 40.

As illustrated, the penile compression device 40 is shown without an occlusive protrusion. It will be appreciated that an occlusive protrusion, such as any of the occlusive protrusions detailed above, may be employed on one of the support arms 44. In a configuration including an occlusive protrusion, the penile compression device 40 may initially be in a slightly deformed position, rather than the adjacently disposed support arms shown in FIGS. 8A-C. The penile compression device 40 may then be further deformed as described to insert a penis and thereby compress a male urethra. It will be appreciated that the presence of an occlusive protrusion, if at all, does not compromise the support arm biasing ability, and suitable urethral compression may be maintained.

In addition to the embodiments described above, various other structures for a penile compression device can be implemented for a penile clamp to achieve desired penile compression. Several additional embodiments are described below. Similar to FIGS. 1A-3B, a one piece clamp structure can include support arms that are joined at their ends by an integrally molded connection (see FIGS. 10A-B below). In other embodiments, the support arms may be joined at their ends by flexible tapes, adhesives, thermal processes, end caps, or through constraint by the absorbent attachment itself (see FIGS. 11A-15B below).

Figure 10A:
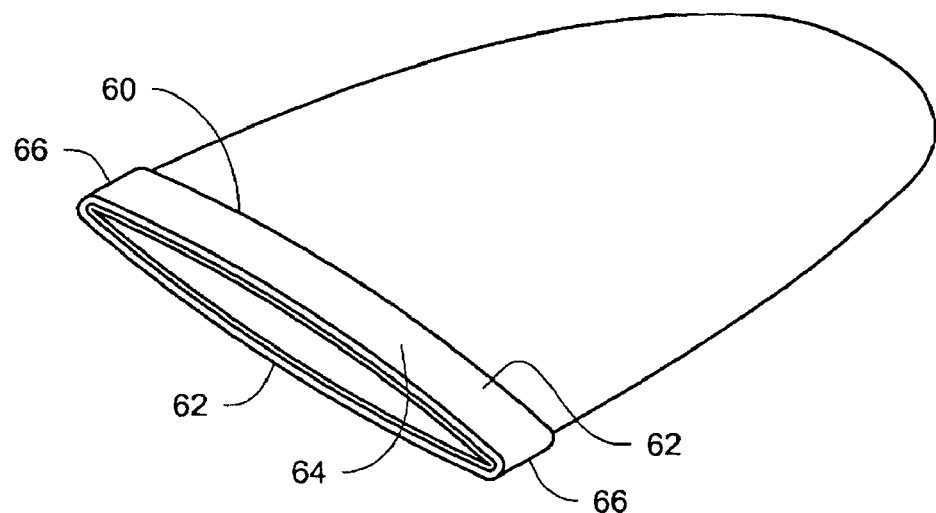
FIGS. 10A-B is another embodiment of a penile compression device showing two support arms that are integrally connected.
Figure 10B:
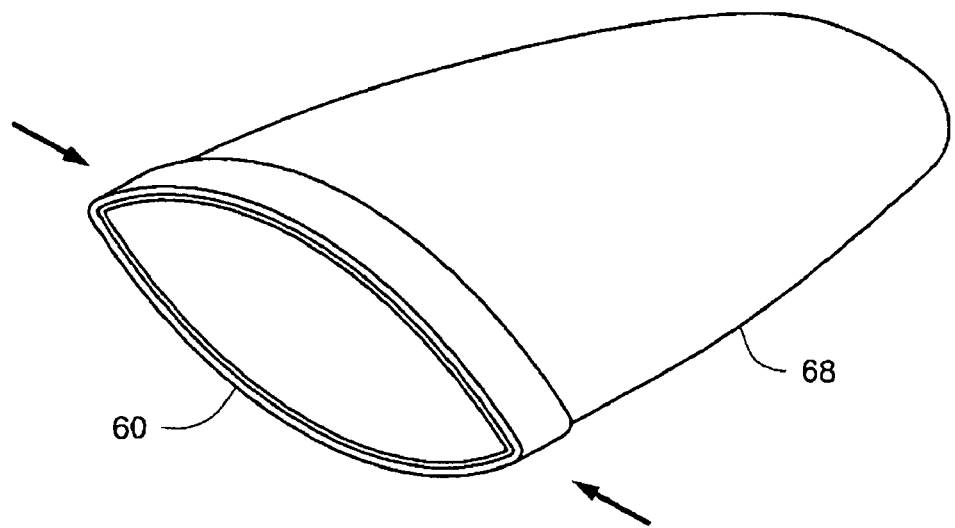

Similar to the embodiment shown in FIGS. 1A-3b, FIGS. 10A and B show a penile clamp 60 that may be formed as a one-piece integral structure. The clamp includes opposing support arms 62 that are integrally formed at ends 66 in a generally closed planar structure 64. The opposing support arms 62 have a spring-like bias established between them to allow compression of the penis and urethra to prevent urinary leakage. As shown in FIG. 10A, the clamp 60 generally has a normally closed position where the support arms 62 biased toward each other. Applying manual force at either end 66 deforms the support arms 62 away from one another to allow insertion of the penis, or to remove compressive force from the penis and remove the clamp (see arrows of FIG. 10B). The spring bias of the support arms 62 is facilitated by junctions between the ends 66 of the support arms 62, which are formed as integral parts of the clamp 60. For example, the nature of the material for the clamp 60 including at least at the ends 66 of the support arms 62 allows for bending when the clamp 60 is compressed from the ends 66, while also allowing the clamp 60 to return to its original normally closed position when compression on the ends 66 is released. FIG. 10A shows the integrally molded connection of the support arms 62, and FIG. 10B shows the clamp in the open position when compressed or flexed.

The clamp may be formed by plastic injection molding or extrusion. Materials which may be employed using these processes include various grades of polycarbonate or acetal thermoplastics. The clamp may also be formed from plastic strips which are thermally formed into the net shape of the clamp. The support arms can be joined at the free ends by adhesives, adhesive tapes or thermal processes such as heat staking or ultrasonic welding (see also following embodiments). Likewise, metal strips may be mechanically bent to the net shape of the clamp and joined at their free ends by adhesives, adhesive tapes or metal welding processes (see also following embodiments). Metals which may be used include, but are not limited to various grades of stainless steel and high carbon steels.

As further shown in FIGS. 1A-B, the clamp 60 may be permanently or removably attached to an absorbent attachment 68. The absorbent attachment 68 may be structured and constructed of materials as similarly described above, where the clamp 60 is attached to the absorbent attachment 68 at the outer surface of an absorbent attachment (shown), on inner surfaces of the absorbent attachment (not shown but see e.g. FIGS. 4A-B), as well as at the end of the absorbent attachment.

Figure 11A:
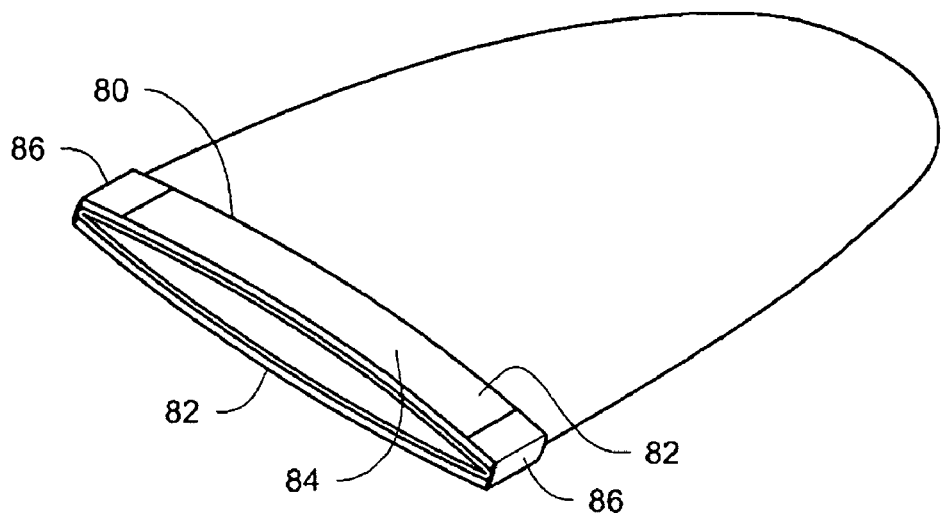
FIGS. 11A-B is another embodiment of penile compression device showing two support arms joined by flexible tapes.
Figure 11B:
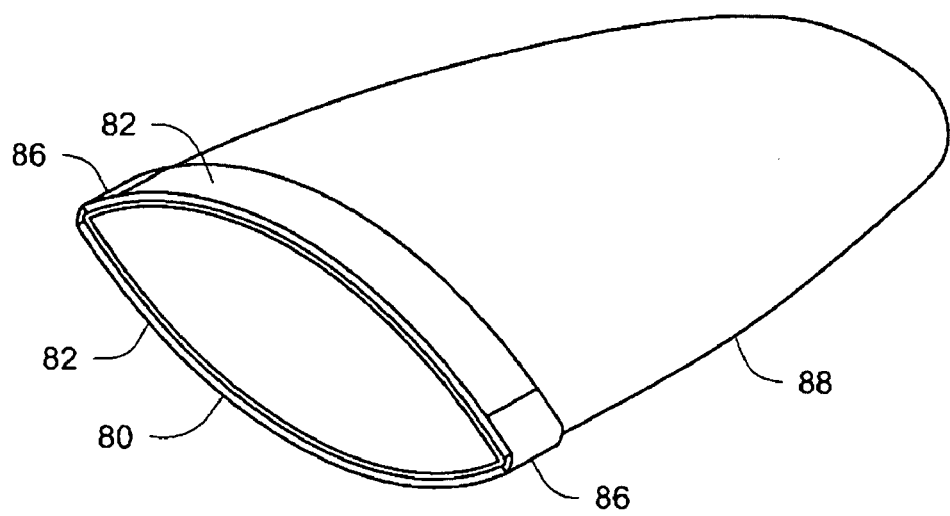

FIGS. 11A-B show another clamp 80, where flexible tapes are employed to join ends of the clamp 80. The clamp 80 includes opposing support arms 82 that are joined at the ends by flexible end tapes 86 so as to form a generally closed planar structure 84. FIG. 11A shows the flexible end tapes 86 at junctions of the support arms 82. The support arms 82 form the clamp 80 when joined at their free ends by the flexible end tapes 86 (see ends of support arms 82 inside the end tapes 86 in FIG. 11B). The flexible end tapes 86 maintain the inward spring bias of the opposing clamp arms 82 by preventing or minimizing the separation of the support arms 82 from one another. In some embodiments, non-reinforced or fabric reinforced adhesive backed tapes can be used as the flexible end tapes 86. As other examples, flexible plastic, rubber, or fabric non-adhesive backed tapes may be employed with attachment between the tapes and support arms being made by a separate application of an adhesive or through a thermal process such as radio frequency or ultrasonic welding.

As above, the support arms 82 may be manufactured from plastic or metal materials. Further shown in FIGS. 11A-B, the clamp 80 may be permanently or removably attached to an absorbent attachment 88. The absorbent attachment 88 may be structured and constructed of materials as similarly described above, and the clamp 80 can be attached to the absorbent attachment 88 at either the outer surface or inner surface of an absorbent attachment, as well as at the end of the absorbent attachment.

Figure 12A:
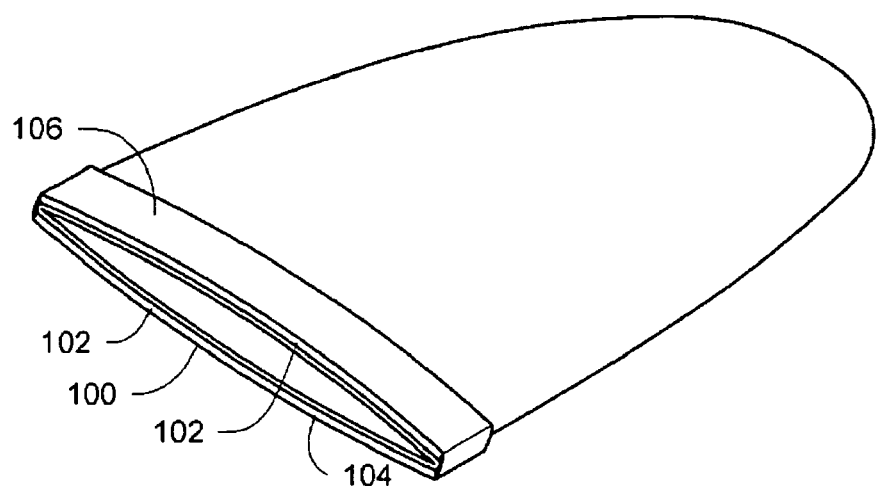
FIGS. 12A-B is another embodiment of a penile compression device showing two support arms joined by a flexible tape wrapped around the support arms.
Figure 12B:
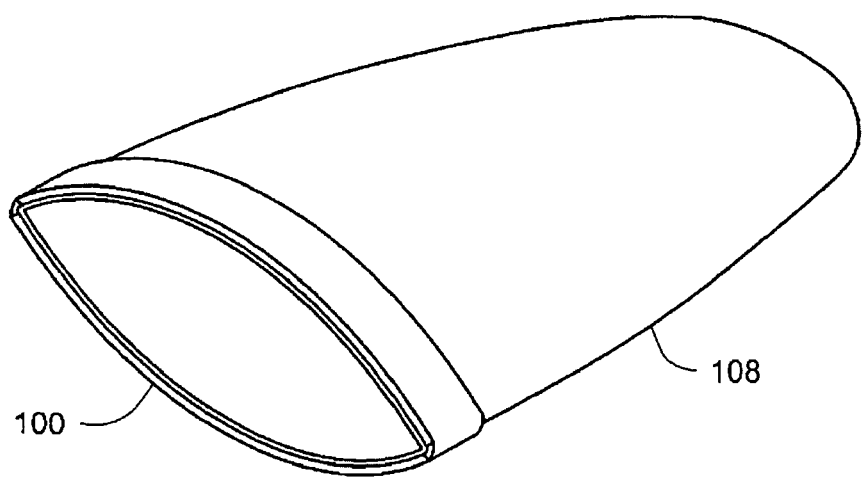

Alternatively, the flexible tape may surround the entire periphery of the clamp. FIGS. 12A-B show another clamp 100, where a flexible tape 106 surrounds the support arms 102 thus surrounding generally the entire outer surface of the clamp 100. The clamp 100 includes opposing support arms 102 that are joined by the flexible tape 106 so as to form a generally closed planar structure 104. The support arms 102 are joined at ends by the flexible tape 106 which wraps around the entire periphery of the clamp 100 and surrounds the outer surface of the support arms 102. In addition to the materials and joining methods already described above, the tape can be held in place using a variety of mechanical structures. As one example hook and loop tape materials such as Velcro® can be used.

As with the previous clamps described, the clamp 100 may be permanently or removably attached to an absorbent attachment 108. The absorbent attachment 108 may be structured and constructed of materials as similarly described above, and the clamp 100 can be attached to the absorbent attachment 108 at either the outer surface or inner surface of an absorbent attachment, as well as at the end of the absorbent attachment.

Figure 13A:
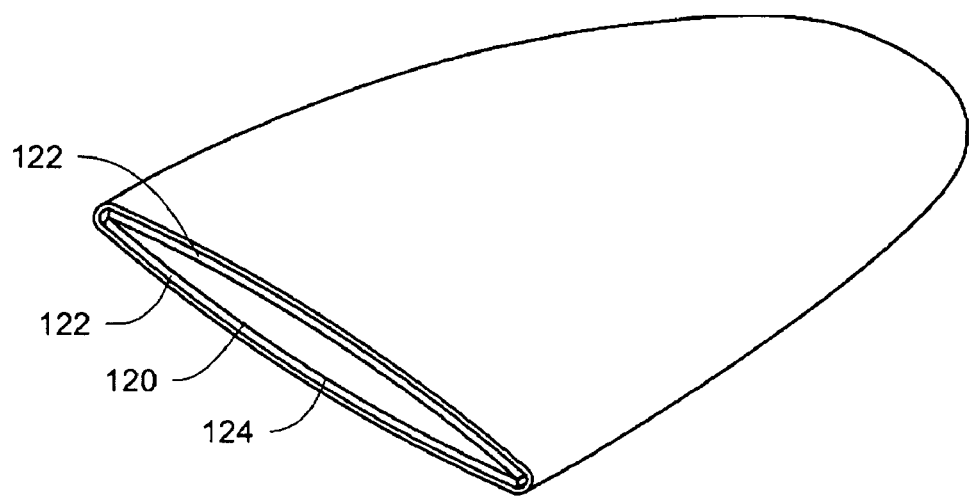
FIGS. 13A-B is another embodiment of a penile compression device, showing two support arms inside an absorbent attachment.
Figure 13B:
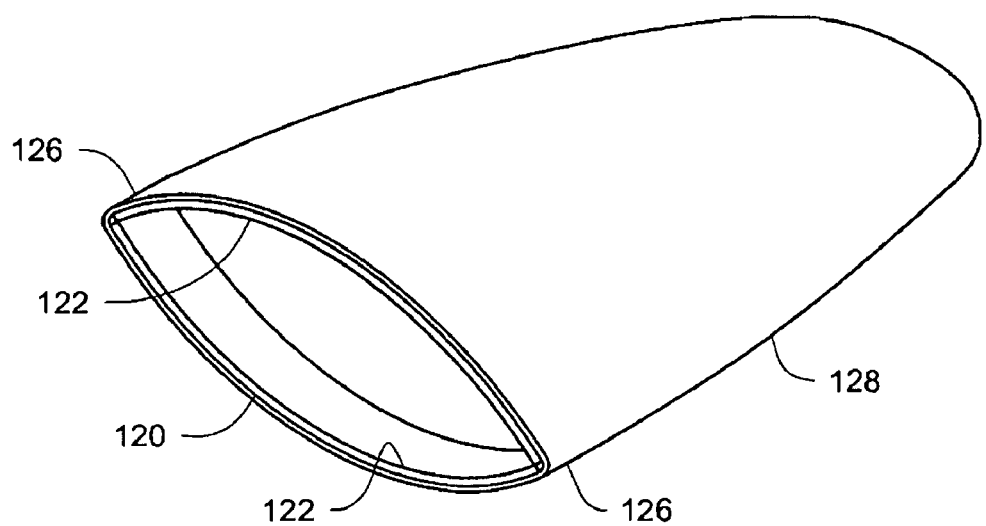

In an attempt to simplify construction of the device and reduce its manufacturing costs, the separate clamp support arms may be held in place and constrained at their mating ends by the walls of the absorbent attachment without the need for tapes. FIGS. 13A-B show another clamp 120 that includes support arms 122 forming a generally closed planar structure 124 by being constrained by walls of an absorbent attachment 128. As shown, the walls of the absorbent attachment 128 generally surround the outer surface of the clamp 120 (shown). FIG. 13A shows the support arms 122 on inside walls of the absorbent attachment 128. FIG. 13B shows the support arm 122 constrained by the walls of the absorbent attachment 128 (see support arm ends inside the clamp). It will be appreciated that the walls of the absorbent attachment can surround the inner surface of the clamp 120 (e.g. support arms 122), for example when the support arms 122 are disposed on an outer surface of the absorbent attachment 128. As one preferred implementation, the walls of the absorbent attachment 128 walls are of sufficient strength to resist the forces imparted by the free ends 126 of the support arms 122.

The absorbent attachment 128 can be structured and constructed of materials that include fabric reinforced materials which have higher tensile strengths to resist loads of the support arm 122, such as when the support arms 122 are compressed.

Figure 14A:
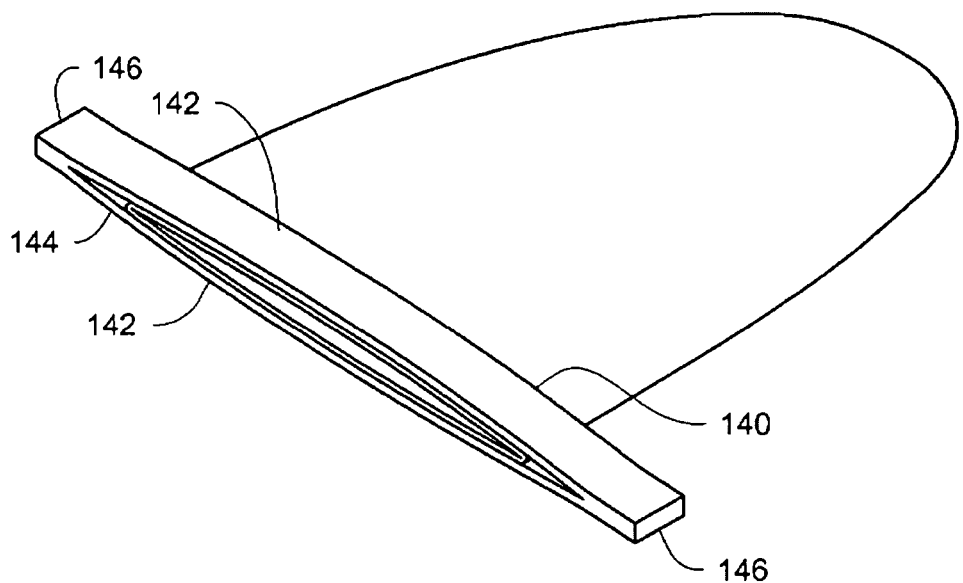
FIGS. 14A-B is another embodiment of a penile compression device showing two support arms attached at the ends by a thermal or adhesive process.
Figure 14B:
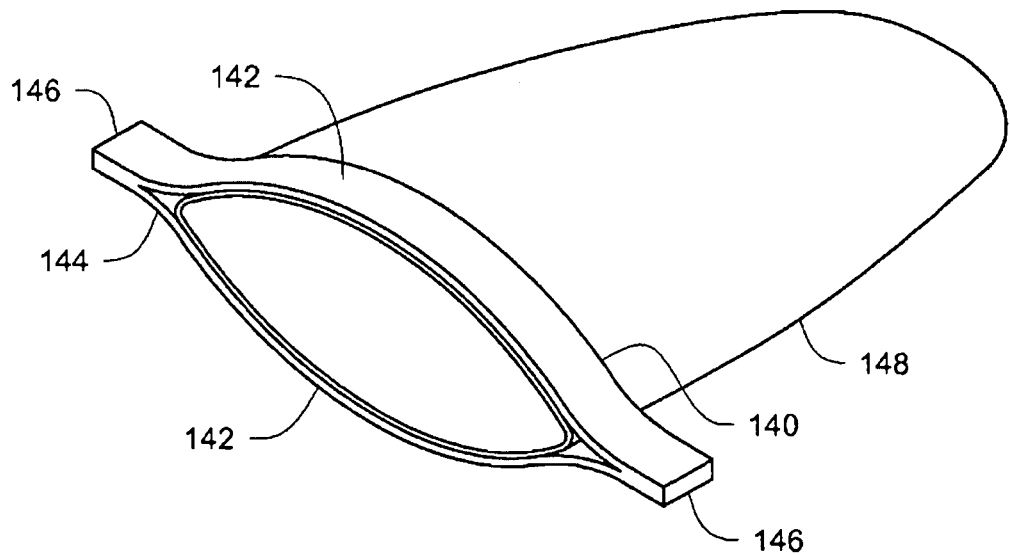

FIGS. 14A-B show another embodiment of a clamp 140. The clamp 140 includes opposing support arms 142 that are formed as a generally closed planar structure 144. The clamp 140 is similarly constructed as clamps 10, 60, but show elongated ends 146 of the support arms 142. In some embodiments, the support arms 142 are joined at free ends 146 through the use of adhesives, radio frequency or ultrasonic welding (plastic support arms) or adhesives, metal welding techniques (metal support arms). In other embodiments, the support arms 142 are attached at ends 146 by a thermal process.

As with the previous clamps described, the clamp 140 may be permanently or removably attached to an absorbent attachment 148. The absorbent attachment 148 may be structured and constructed of materials as similarly described above, and the clamp 140 can be attached to the absorbent attachment 148 at either the outer surface or inner surface of an absorbent attachment, as well as at the end of the absorbent attachment.

Figure 15A:
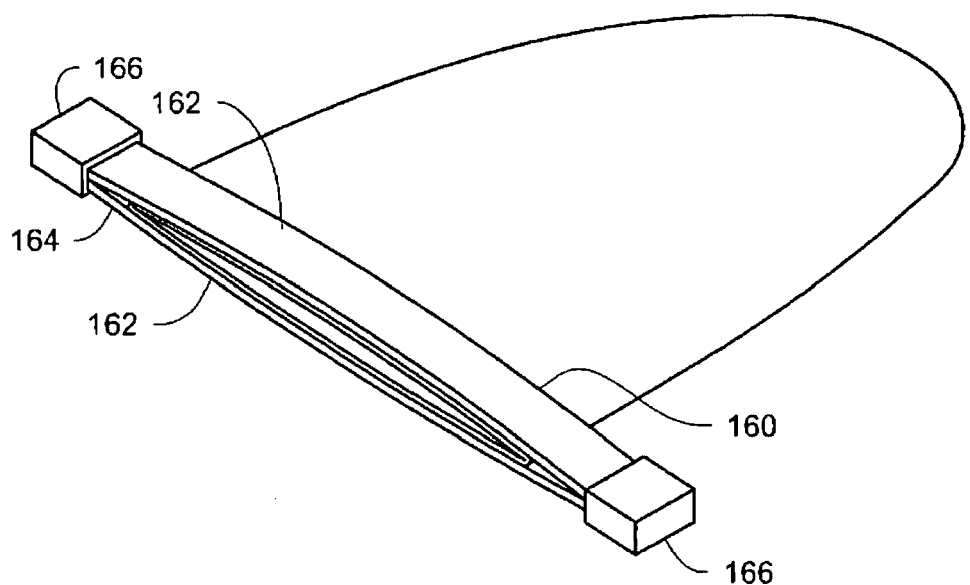
FIGS. 15A-B is another embodiment of a penile compression device showing two support arms joined at the ends by end caps.
Figure 15B:
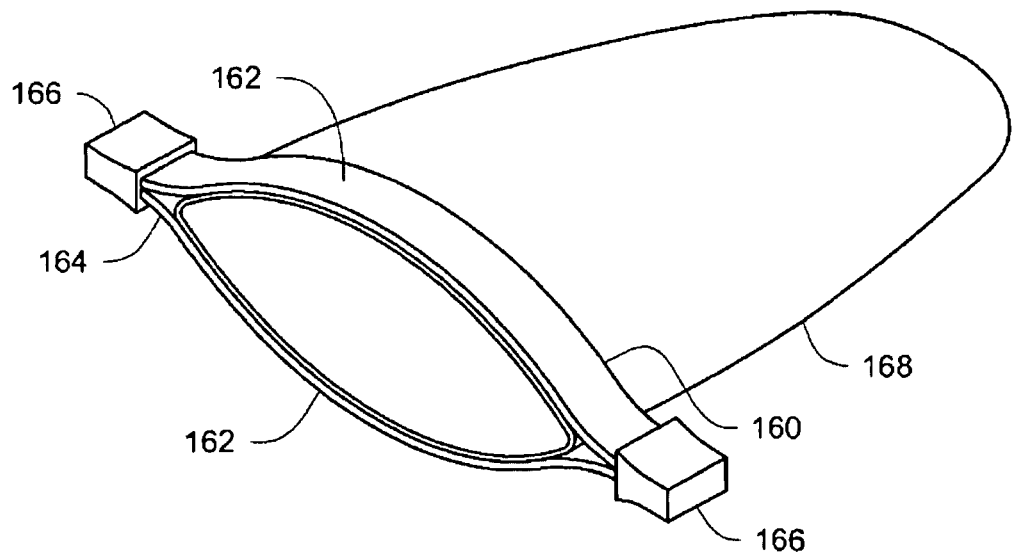

FIGS. 15A-B show another embodiment of a clamp 160. The clamp 160 includes opposing support arms 162 that are formed as a generally closed planar structure 164 by using end caps 166. As shown, the free ends of the support arms 162 are constrained and held together by end caps 166. In one preferred implementation, the end caps 166 are elastomeric and can stretch as the clamp is deformed (e.g. compressed to open state, see FIG. 15B) and returns to its original shape when compression of the clamp 160 is released and the clamp is allowed to return to its unstressed state. In some embodiments, the end caps 166 may be manufactured from, but are not limited to, materials such as silicone or butyl rubber and polyurethane.

As with the previous clamps described, the clamp 160 may be permanently or removably attached to an absorbent attachment 168. The absorbent attachment 168 may be structured and constructed of materials as similarly described above, and the clamp 160 can be attached to the absorbent attachment 168 at either the outer surface or inner surface of an absorbent attachment, as well as at the end of the absorbent attachment.

While the above clamps in FIGS. 10A-15B do not show an occlusive protrusion, it will be appreciated that any of the clamps described may incorporate the use of an occlusive protrusion according to the principles described. Likewise, the clamps of FIGS. 10B-15B can incorporate the use of any of the absorbent attachments, sleeves already described and can incorporate the use of an additional padding material (e.g. padding material 48) on the support arms. Even further, any of the clamps of FIGS. 10A-15B can be used in conjunction with the pressure concentrating inserts (e.g. pressure concentrating inserts 19, 59) already described.

The penile compression device and the above provide suitable neurovascular load distribution that can be coupled with localized urethral compression. The penile compression device provides a universally fitting clamp that improves comfort and is user friendly, while improving urine leakage prevention.

Applicants provide some of the following examples of uses for the devices and methods described herein.

Uses

Stress Urinary Incontinence

As discussed above, the devices and methods described herein can be used by men suffering from stress urinary incontinence (SUI) which is the involuntary loss of urine during activities such as coughing, sneezing, laughing or exercising. Alternate uses have been identified which include bladder training and anesthetic retention.

Bladder Training

The symptoms of SUI may vary from minor, occasional leakage to a complete inability to retain urine in the bladder. In this more extreme instance, the bladder is never stretched to its full capacity and gradually atrophies which further limits its urine storage capability. A bladder training program may be employed where by the patient wears any of the devices described herein and optionally with an absorbent attachment for several hours at a time. In so doing, urine can be prevented from leaving the bladder and the bladder walls are stretched. A repeated program of bladder stretching exercises can reshape the bladder and return lost urine storage capacity.

Anesthetic Retention

Passage of catheters, urethroscopes and cystoscopes through the male urethra is often preceded by instillation of an anesthetic agent into the urethral lumen. Retention of this anesthetic agent can be accomplished by placing any of the devices described herein and optionally with an absorbent attachment over the distal end of the penis to prevent anesthetic leakage. Holding the anesthetic within the urethra for a period of 10 to 30 minutes can be sufficient to effect an anesthetic effect and allow relatively pain free passage of the catheter or scope.

The above specification provides a complete description of the composition, manufacture and use of the improved penile compression device in accordance with the principles of the present invention. Since many embodiments of the invention can be made without departing from the spirit and scope of the invention, the invention resides in the claims hereinafter appended.

The invention claimed is:

1. A penile compression device, comprising:
   a first semi-rigid support arm;
   a second semi-rigid support arm, the first and second semi-rigid support arms being connected at opposing ends of a length direction thereof, the semi-rigid support arms being biased toward each other in a resting position, and are compressible from the length direction such that the semi-rigid support arms are deformable away from each other,
   the first and second semi-rigid support arms have an open region formed between the first and second semi-rigid support arms when deformed, the open region enabling penis insertion between the semi-rigid support arms, and releasing compression of the first and second semi-rigid support arms enabling the semi-rigid support arms to bias from a deformed position to a clamp position, whereby the semi-rigid support arms bias toward each other to compress a male urethra and prevent urinary leakage; and
   an absorbent attachment connected to the first and second semi-rigid support arms, the absorbent attachment capturing and holding inadvertent urine leakage, and
   the first and second semi-rigid support arms being connected at opposing ends by one of:
      an integrally formed connection, where the opposing ends are integrally formed so that the first and second semi-rigid support arms are a single, unitary structure;
      flexible tapes disposed on the opposing ends;
      a flexible tape disposed around the outer surface of the first and second semi-rigid support arms;
      end caps disposed over the opposing ends; and
      walls of the absorbent attachment that contact the first and second semi-rigid support arms and that constrain the first and second semi-rigid support arms.

2. The penile compression device according to claim 1, wherein one of the first and second semi-rigid support arms including an occlusive protrusion disposed on an inner side surface thereof, the occlusive protrusion capable of concentrating compression on a male urethra when the first and second semi-rigid support arms are biased toward each other.

3. The penile compression device according to claim 1, wherein each of the first and second semi-rigid support arms including a foam disposed on an inner side surface thereof.

4. The penile compression device according to claim 1, wherein the first and second semi-rigid support arms are an injection molded material.

5. The penile compression device according to claim 1, wherein each of the first and second semi-rigid support arms are flat and form a planar shape.

6. The penile compression device according to claim 1, wherein the absorbent attachment is a sleeve enabling penis insertion therein, the sleeve is configured to envelop the penis and contain inadvertent urine leakage.

7. The penile compression device according to claim 1, wherein absorbent attachment is attached to outer surfaces of the first and second semi-rigid support arms or inner surfaces of the first and second semi-rigid support arms.

8. The penile compression device according to claim 1, wherein the absorbent attachment is disposed through the opening of the first and second semi-rigid support arms, such that the semi-rigid support arms are slidable over the absorbent attachment and are configured to anchor the absorbent attachment, when the absorbent attachment is placed onto the penis and when the semi-rigid support arms are in the clamp position.

9. The penile compression device according to claim 1, further comprising a pressure concentrating insert, the pressure concentrating insert is surgically implanted on a dorsal urethral surface.

10. The penile compression device according to claim 9, wherein the pressure concentrating insert including a width along a urethral axis that is equivalent to a width of the occlusive protrusion.

11. The penile compression device according to claim 9, wherein the pressure concentrating insert having an arcuate shape and substantially contouring the dorsal urethral surface.

12. The penile compression device according to claim 1, further comprising a deforming position when the first and second semi-rigid support arms are compressed from the length direction such that the semi-rigid support arms are deformed away from each other so as to allow insertion or removal of a penis between the semi-rigid support arms.

13. A penile compression device, comprising:
   a first semi-rigid support arm;
   a second semi-rigid support arm, the first and second semi-rigid support arms being connected at opposing ends of a length direction thereof, the semi-rigid support arms being biased toward each other in a resting position, and are compressible from the length direction such that the semi-rigid support arms are deformable away from each other,
   the first and second semi-rigid support arms have an open region formed between the first and second semi-rigid support arms when deformed, the open region enabling penis insertion between the semi-rigid support arms, and releasing compression of the first and second semi-rigid support arms enabling the semi-rigid support arms to bias from a deformed position to a clamp position, whereby the semi-rigid support arms bias toward each other to compress a male urethra and prevent urinary leakage; and
   an absorbent attachment connected to the first and second semi-rigid support arms, the absorbent attachment capturing and holding inadvertent urine leakage,
   the first and second semi-rigid support arms being connected at opposing ends by one of:
      an integrally formed connection, where the opposing ends are integrally formed so that the first and second semi-rigid support arms are a single, unitary structure;
      flexible tapes disposed on the opposing ends;
      a flexible tape disposed around the outer surface of the first and second semi-rigid support arms;
      end caps disposed over the opposing ends; and
      walls of the absorbent attachment that contact the first and second semi-rigid support arms and that constrain the first and second semi-rigid support arms
   wherein the absorbent attachment is releasable from connection with the first and second semi-rigid support arms.

* * * * *